US009044436B2

(12) United States Patent
Chuang et al.

(10) Patent No.: US 9,044,436 B2
(45) **Date of Patent: *Jun. 2, 2015**

(54) COMPOSITIONS AND METHODS FOR THE TREATMENT OF ANGIOGENESIS-RELATED EYE DISEASES

(75) Inventors: Woei-Jer Chuang, Tainan (TW); Wen-Mei Fu, Taipei (TW); Yen-Lun Huang, Taoyuan County (TW)

(73) Assignees: National Cheng Kung University, Tainan (TW); National Taiwan University, Taipei (TW)

( * ) Notice: Subject to any disclaimer, the term of this patent is extended or adjusted under 35 U.S.C. 154(b) by 848 days.

This patent is subject to a terminal disclaimer.

(21) Appl. No.: 12/975,630

(22) Filed: Dec. 22, 2010

(65) Prior Publication Data

US 2011/0152192 A1 Jun. 23, 2011

Related U.S. Application Data

(60) Provisional application No. 61/289,624, filed on Dec. 23, 2009.

(51) Int. Cl.

*A61K 38/00* (2006.01)
*C07K 14/78* (2006.01)
*A61K 38/17* (2006.01)
*A61K 47/48* (2006.01)

(52) U.S. Cl.

CPC ....... *A61K 38/1703* (2013.01); *A61K 47/48284* (2013.01)

(58) Field of Classification Search

None

See application file for complete search history.

(56) References Cited

U.S. PATENT DOCUMENTS

| | | | | |
|---|---|---|---|---|
| 4,179,337 | A | 12/1979 | Davis et al. | |
| 4,301,144 | A | 11/1981 | Iwashita et al. | |
| 4,496,689 | A | 1/1985 | Mitra | |
| 4,640,835 | A | 2/1987 | Shimizu et al. | |
| 4,670,417 | A | 6/1987 | Iwasaki et al. | |
| 4,791,192 | A | 12/1988 | Nakagawa et al. | |
| 6,710,030 | B1 | 3/2004 | Markland et al. | |
| 6,974,884 | B2 | 12/2005 | Raines et al. | |
| 7,943,728 | B2 * | 5/2011 | Chuang et al. | 530/300 |
| 2007/0025957 | A1 * | 2/2007 | Rosenblum et al. | 424/85.1 |
| 2008/0188413 | A1 * | 8/2008 | Chuang et al. | 514/12 |
| 2011/0015130 | A1 * | 1/2011 | Chuang et al. | 514/15.2 |

FOREIGN PATENT DOCUMENTS

| | | | |
|---|---|---|---|
| WO | WO 95/34326 | A1 | 12/1995 |
| WO | WO 2008088548 | A2 * | 7/2008 |

OTHER PUBLICATIONS

International Search Report and Written Opinion, dated Aug. 8, 2008.

Yang R., et al., "Rhodostomin inhibits thrombin-enhanced adhesion of ROS 17/2.8 cells through the blockade of αvβ3 integrin," Toxicon., Jul. 2005, vol. 46, No. 4, pp. 387-393.

Chang, H.H., et al., "Rhodostomin, an RGD-containing peptide expressed from a synthetic gene in *Escherichia coli*, facilitates the attachment of human hepatoma cells," Biochem Biophys Res Commun., Jan. 1993, vol. 190, No. 1, pp. 242-249.

Crippes, B.A., et al., "Antibody to β3 integrin inhibits osteoclast-mediated bone resorption in the thyroparathyroidectomized rat," Endocrinology, Mar. 1996, vol. 137, No. 3, pp. 918-924.

Dejana E., et al., "Bleeding time in rats: a comparison of different experimental conditions," Thromb Haemost., Aug. 1982, vol. 48, No. 1., pp. 108-111.

Engleman, V.W., et al., "A peptidomimetic antagonist of the alpha(v)beta3 integrin inhibits bone resorption in vitro and prevents osteoporosis in vivo," J Clin Invest, May 1997, vol. 99, No. 9, pp. 2284-2292.

Goltzman, D. "Discoveries, drugs and skeletal disorders," Nat Rev Drug Discov, Oct. 2002, vol. 1, No. 10, pp. 784-796.

Gould, R.J., et al., "Disintegrins: a family of integrin inhibitory proteins from viper venoms," Proc Soc Exp Biol Med, Nov. 1990, vol. 195, No. 2, pp. 168-171.

Horton, M.A., et al., "Arg-gly-asp (RGD) peptides and the anti-vitronectin receptor antibody 23C6 inhibit dentine resorption and cell spreading by osteoclasts," Exp Cell Res, Aug. 1991, vol. 195, No. 2. pp. 368-375.

Huang, T.F., "What have snakes taught us about integrins?," Cell Mol Life Sci, Jun. 1998, vol. 54, No. 6, pp. 527-540.

Huang, T.F., et al., "Rhodostomin, a snake venom peptide and its fragment inhibit platelet aggregation by acting as fibrinogen receptor antagonist," 11th International Congress on Thrombosis; Ljubljana, Yugoslavia, Jun. 1990, Abstract 141.

Hunkapiller M., et al., "A microchemical facility for the analysis and synthesis of genes and proteins," Nature, Jul. 1984, vol. 310, No. 5973, pp. 105-111.

Inoue, M., et al., "GM-CSF regulates expression of the functional integrins αvβ3 and αvβ5 in a reciprocal manner during osteoclastogenesis," J Bone Miner Res, 1995, vol. 10, p. S163a. (Abstr.).

Lin, Y.T., et al., "Inhibition of adipogenesis by RGD-dependent disintegrin," Biochemical Pharmacology, Nov. 2005, vol. 70, No. 10, pp. 1469-1478.

Mimura, H., et al., "1,25(OH)2D3 vitamin D3 transcriptionally activates the β3-integrin subunit gene in avian osteoclast precursors," Endocrinology, Mar. 1994, vol. 134, No. 3, pp. 1061-1066.

Miyauchi, A.J., et al., "Recognition of osteopontin and related peptides by an αvβ3 integrin stimulates immediate cell signals in osteoclasts," J Biol Chem, Oct. 1991, vol. 266, No. 30, pp. 20369-20374.

(Continued)

*Primary Examiner* — James H Alstrum Acevedo
*Assistant Examiner* — Li Lee
(74) *Attorney, Agent, or Firm* — Wood, Phillips, Katz, Clark & Mortimer

(57) ABSTRACT

The invention generally relates to compositions and methods of treatment and/or prevention of angiogenesis-related eye diseases using low doses of rhodostomin variants, and in particular, low doses of a fusion protein comprising a rhodostomin variant, wherein the rhodostomin variant is conjugated with a variant of Human Serum Albumin (HSA) where the cysteine residue at position 34 of the HSA amino acid sequence has been replaced with serine.

10 Claims, 7 Drawing Sheets

(56) References Cited

OTHER PUBLICATIONS

Monfardini, C., et al., "A branched monomethoxypoly(ethylene glycol) for protein modification," Bioconjugate Chem., Jan.-Feb. 1995, vol. 6, No. 1, pp. 62-69.
Mundy, G.R. "Mechanisms of osteolytic bone destruction," Bone, 1991, Supplement, pp. S1-S6.
Mundy, G.R., "Metastasis to bone: causes, consequences and therapeutic opportunities," Nat Rev Cancer, Aug. 2002, vol. 2, No. 8, pp. 584-593.
Nakamura, I., et al., "Echistatin inhibits the migration of murine prefusion osteoclasts and the formation of multinucleated osteoclast-like cells," Endocrinology, Dec. 1998, vol. 139, No. 12, pp. 5182-5193.
Passaniti A., et al., "A simple, quantitative method for assessing angiogenesis and antiangiogenic agents using reconstituted basement membrane, heparin, and fibroblast growth factor," Lab. Invest., Oct. 1992, vol. 67, No. 4, pp. 519-528.
Ross, F.P., et al., "Interactions between the bone matrix proteins osteopontin and bone sialoprotein and the osteoclast integrin $\alpha v\beta 3$ potentiate bone resorption," J Biol Chem, May 1993, vol. 268, No. 13, pp. 9901-9907.
Sato K., Takayanagi H. "Osteoclasts, rheumatoid arthritis and osteoimmunology," Curr. Opin. Rheumatol., Jul. 2006, vol. 18, No. 4, pp. 419-426.
Stefano et al., "A conjugate of doxorubicin with lactosaminated albumin enhances the drug concentrations in all the forms of rat hepatocellular carcinomas independently of their differentiation grade," Liver Int., Aug. 2006, vol. 26, No. 6, pp. 726-733.
Tanaka, S., "Signaling axis in osteoclast biology and therapeutic targeting in the RANKL/RANK/OPG System," Am. J. Nephrol, 2007, vol. 27, No. 5, pp. 466-478.
Tang C.H., et al., "Enhancement of fibronectin fibrillogenesis and bone formation by basic fibroblast growth factor via protein kinase C-dependent pathway in rat osteoblasts," Mol Pharmacol., Sep. 2004, vol. 66, No. pp. 440-449.
Turner C.H., Burr D.B., "Basic biomechanical measurements of bone: a tutorial," Bone, Jul.-Aug. 1993, vol. 14, No. 4, pp. 595-608.
Turner C.H., et al., "The effects of fluoridated water on bone strength," Orthop Res, Jul. 1992, vol. 10, No. pp. 581-587.
Van Der Heijde D.M., et al., "Radiographic progression on radiographs of hands and feet during the first 3 years of rheumatoid arthritis measured according to sharp's method (van der Heijde modification)," J. Rheumatol., Sep. 1995; vol. 22, No. 9, pp. 1792-1796.
Van't Hof, R.J., Ralston, S.H., "Nitric oxide and bone," Immunology, Jul. 2001, vol. 103., No. 3, pp. 255-261.
Weinreb M., et al., "Depression of osteoblastic activity in immobilized limbs of suckling rats," J Bone Miner Res., Jul. 1991, vol. 6, No. 7, pp. 725-731.
Wilkinson-Berka, J.L., et al., "COX-2 inhibition and retinal angiogenesis in a mouse model of retinopathy of prematurity," Invest Ophthalmol Vis Sci., Mar. 2003, vol. 44, No. 3, pp. 974-979.
Yang R., et al., "Differential effects of bone mineral content and bone area on vertebral strength in a swine model," Calcif Tissue Int., Jul. 1998, vol. 63, No. 1, pp. 86-90.
Yang, R.S., et al., "Inhibition of tumor formation by snake venom disintegrin," Toxicon., Apr. 2005, vol. 45, No. 5, pp. 661-669.
Yeh, C.H., et al., "Rhodostomin, a snake venom disintegrin, inhibits angiogenesis elicited by basic fibroblast growth factor and suppresses tumor growth by a selective $\alpha v\beta 3$ blockade of endothelial cells," Mol Pharmacol., May 2001, vol. 59, No. 5, pp. 1333-1342.
Yoneda, T., et al., "Bone-seeking clone exhibits different biological properties from the MDA-MB-231 parental human breast cancer cells and a brain-seeking clone in vivo and in vitro," J Bone Miner Res, Aug. 2001, vol. 16, No. 8, pp. 1486-1495.
Zallipsky, S., "Functionalized poly(ethylene glycol) for the preparation of biologically relevant conjugates," Bioconjugate Chem., Mar.-Apr. 1995, vol. 6, No. 2, pp. 150-165.
Zhang, X.P., et al., "Specific interaction of the recombinant disintegrin-like domain of MDC-15 (metargidin, ADAM-15) with integrin alphavbeta3," J Biol Chem, Mar. 1998, vol. 273, No. 13, pp. 7345-7350.
Office Action issued in corresponding Japanese application No. 2012-546185 issued Dec. 2, 2014.
Zhou et al., "Elimination of the free sulfhydryl group in the human serum albumin (HAS) moiety of human interferon-$\alpha$2b and HAS fusion protein increases its stability against mechanical and thermal stresses", European Journal of Pharmaceuticals and Biopharmaceutics, 72 (2009), pp. 405-411.

* cited by examiner

Inhibition of Angiogenesis in Retina by ARLDDL and HSA-ARLDDL

Inhibition of Angiogenesis in Retina by HSA-ARLDDL

Inhibition of Angiogenesis in Retina by HSA-ARLDDL

COMPOSITIONS AND METHODS FOR THE TREATMENT OF ANGIOGENESIS-RELATED EYE DISEASES

FIELD OF THE INVENTION

The present invention generally relates to compositions and methods utilizing low doses of disintegrin variants for the treatment and/or prevention of angiogenesis-related eye diseases.

BACKGROUND OF THE INVENTION

Integrins are heterodimeric matrix receptors that anchor cells to substrates and transmit externally derived signals across the plasma membrane. Integrin αvβ3 is a type of integrin that is a receptor for vitronectin. Integrin αvβ3 is expressed at low levels in most normal cells including intestinal, vascular, and smooth muscle cells. The cell types that express high levels of this heterodimer molecular include bone-resorbing osteoclasts, activated macrophages, a small fraction of neutrophils, angiogenic endothelial cells and migrating smooth muscle cells. Integrin αvβ3 is involved in the osteoclast-mediated bone resorption, both in vivo and in vitro, as well as new blood vessel formation. This heterodimer molecule recognizes the amino acid motif Arg-Gly-Asp (RGD) contained in bone matrix proteins such as osteopontin and bone sialoprotein.

Disintegrins are a family of low-molecular-weight RGD-containing peptides that bind specifically to integrins αIIbβ3, α5β1 and αvβ3 expressed on platelets and other cells including vascular endothelial cells and some tumor cells.

Various disintegrins are known in the art, including rhodostomin and its variants, including but not limited to ARLDDL.

Angiogenesis-related eye diseases are eye diseases which are related to the growth of new blood vessels from pre-existing vessels. These diseases include but are not limited to, age-related macular degeneration, diabetic retinopathy, corneal neovascularizing diseases, retinal angiomatous proliferation, polypoidal choroidal vasculopathy, ischaemia-induced neovascularizing retinopathy, high myopia and retinopathy of prematurity.

Because existing drugs are not satisfactorily effective in the treatment of angiogenesis-related eye diseases, there is a need for novel treatments of these diseases.

SUMMARY OF THE INVENTION

Generally, the invention relates to compositions and methods for the treatment and/or prevention of an angiogenesis-related eye disease utilizing low doses of rhodostomin variants.

The term "low doses" refers to the doses which are lower than those conventionally used for the treatment of an angiogenesis-related eye disease.

Preferably, "low doses" are from about 0.0001 pg to about 300 ug per eye; more preferably, from about 0.005 pg to about 200 ug per eye, and even more preferably, from about 0.001 pg to about 100 ug per eye of the rhodostomin variants suitable for the purposes of the present invention. The doses can be administered to a subject in need thereof as once weekly, once monthly, once quarterly or once yearly doses.

Preferably, said rhodostomin variants are fused with human serum albumin (HSA) or variants of HSA. As used throughout the application, the term "rhodostomin variant" encompasses a rhodostomin variant fused with HSA or an HSA variant which may be pegylated or otherwise modified.

Rhodostomin variants suitable for use in the present invention comprise an amino acid sequence selected from SEQ ID NO: 1 through SEQ ID NO: 16 or a pharmaceutically acceptable salt of said rhodostomin variant.

SEQ ID NO: 1 represents an amino acid sequence of "ARGDDP" rhodostomin variant, which is a rhodostomin variant having an RGD motif variant $^{48}$ARGDDP$^{53}$.

SEQ ID NO: 2 represents an amino acid sequence of "ARGDDV" rhodostomin variant, which is a rhodostomin variant having an RGD motif variant $^{48}$ARGDDV$^{53}$.

SEQ ID NO: 3 represents an amino acid sequence of "ARGDDL" rhodostomin variant, which is a rhodostomin variant having an RGD motif variant $^{48}$ARGDDL$^{53}$.

SEQ ID NO: 4 represents an amino acid sequence of "PRGDDL" rhodostomin variant, which is a rhodostomin variant having an RGD motif variant $^{48}$PRGDDL$^{53}$.

SEQ ID NO: 5 represents an amino acid sequence of "ARGDDM" rhodostomin variant, which is a rhodostomin variant having an RGD motif variant $^{48}$ARGDDM$^{53}$.

SEQ ID NO: 6 represents an amino acid sequence of "PRGDDM" rhodostomin variant, which is a rhodostomin variant having an RGD motif variant $^{48}$PRGDDM$^{53}$.

SEQ ID NO: 7 represents an amino acid sequence of "PRLDMP" rhodostomin variant, which is a rhodostomin variant having an RGD motif variant $^{48}$PRLDMP$^{53}$.

SEQ ID NO: 8 represents an amino acid sequence of "PRLDDL" rhodostomin variant, which is a rhodostomin variant having an RGD motif variant $^{48}$PRLDDL$^{53}$.

SEQ ID NO: 9 represents an amino acid sequence of "ARLDDL" rhodostomin variant, which is a rhodostomin variant having an RGD motif variant $^{48}$ARLDDL$^{53}$.

SEQ ID NO: 10 represents an amino acid sequence of "PRIDMP" rhodostomin variant, which is a rhodostomin variant having an RGD motif variant $^{48}$PRIDMP$^{53}$.

SEQ ID NO: 11 represents an amino acid sequence of "PRHDMP" rhodostomin variant, which is a rhodostomin variant having an RGD motif variant $^{48}$PRHDMP$^{53}$.

SEQ ID NO: 12 represents an amino acid sequence of "PRGDNP" rhodostomin variant, which is a rhodostomin variant having an RGD motif variant $^{48}$PRGDNP$^{53}$.

SEQ ID NO: 13 represents an amino acid sequence of "PRGDGP" rhodostomin variant, which is a rhodostomin variant having an RGD motif variant $^{48}$PRGDGP$^{53}$.

SEQ ID NO: 14 represents an amino acid sequence of "ARLDDL" rhodostomin variant conjugated with HSA.

SEQ ID NO: 15 represents an amino acid sequence of "ARLDDL" rhodostomin variant conjugated with an HSA variant, wherein the cysteine residue at position 34 of wild type HSA amino acid sequence has been replaced with serine. The rhodostomin variant represented by SEQ ID NO: 15 may also be referred to as HSA(C34S)-ARLDDL fusion protein. The protein is a fusion product of: a) an HSA variant wherein the cysteine residue at position 34 of the HSA amino acid sequence has been replaced with serine, b) a linker amino acid sequence and c) ARLDDL rhodostomin variant.

SEQ ID NO: 16 represents an amino acid sequence of "ARLDDL" rhodostomin variant conjugated with an HSA variant, wherein the cysteine residue at position 34 of wild type HSA amino acid sequence has been replaced with alanine.

Accordingly, in one embodiment, the invention relates to a composition for the treatment and/or prevention of an angiogenesis-related eye disease comprising from about 0.0001 pg to about 300 ug of a rhodostomin variant comprising an amino acid sequence selected from SEQ ID NO: 1 through SEQ ID NO: 16, or a pharmaceutically acceptable salt of said rhodostomin variant.

Most preferably, the rhodostomin variants suitable for the purposes of the present invention comprise SEQ ID NO: 9 or SEQ ID NO: 15.

Preferably, the compositions of the invention comprise from about 0.005 pg to about 200 ug, and more preferably, from about 0.001 pg to about 100 ug of the rhodostomin variant suitable for the purposes of the invention.

In one embodiment, the compositions of the invention are formulated as topical compositions. In another embodiment, the compositions of the invention are suitable for an intraocular injection (i.e., into the eye).

In another embodiment, the invention relates to a method for the treatment and/or prevention of an angiogenesis-related eye disease comprising administering to a subject in need thereof from about 0.0001 pg to about 300 ug per eye of said subject of a rhodostomin variant comprising an amino acid sequence selected from SEQ ID NO: 1 through SEQ ID NO: 16, or a pharmaceutically acceptable salt of said rhodostomin variant.

In a preferred embodiment, the invention relates to a method for the treatment and/or prevention of an angiogenesis-related eye disease comprising administering to a subject in need thereof from about 0.0001 pg to about 300 ug per eye of said subject of a rhodostomin variant comprising an amino acid sequence selected from SEQ ID NO: 9 and SEQ ID NO: 15, or a pharmaceutically acceptable salt of said rhodostomin variant.

In a more preferred embodiment, the invention relates to a method for the treatment and/or prevention of an angiogenesis-related eye disease comprising administering to a subject in need thereof from about 0.0005 pg to about 200 ug per eye of said subject of a rhodostomin variant comprising an amino acid sequence selected from SEQ ID NO: 1 through SEQ ID NO: 16, or a pharmaceutically acceptable salt of said rhodostomin variant.

In an even more preferred embodiment, the invention relates to a method for the treatment and/or prevention of an angiogenesis-related eye disease comprising administering to a subject in need thereof from about 0.001 pg to about 100 ug per eye of said subject of a rhodostomin variant comprising an amino acid sequence selected from SEQ ID NO: 1 through SEQ ID NO: 16, or a pharmaceutically acceptable salt of said rhodostomin variant.

Preferably, the methods of the invention comprise administering from about 0.005 pg to about 300 ug, and more preferably, from about 0.001 pg to about 100 ug of the rhodostomin variant suitable for the purposes of the invention per eye of said subject.

In one embodiment, the methods of the invention comprise administering the rhodostomin variant suitable for the purposes of the invention through an intravitreous injection to said subject.

In one embodiment, the angiogenesis-related eye disease is selected from the group consisting of age-related macular degeneration (AMD), diabetic retinopathy, corneal neovascularizing diseases, retinal angiomatous proliferation, polypoidal choroidal vasculopathy, age-related ischaemia-induced neovascularizing retinopathy, high myopia and retinopathy of prematurity.

In another embodiment, the methods of the invention further comprise administering a therapeutically effective amount of another active agent. The other active agent may be administered before, during, or after administering the rhodostomin variant suitable for the purposes of the invention.

Preferably, the other active agent is selected from the group consisting of VEGF antagonists, anti-angiogenesis agents, anti-inflammation agents, and steroids.

The compositions of the present invention may further include a pharmaceutically acceptable carrier.

These and other aspects will become apparent from the following description of the various embodiments taken in conjunction with the following drawings, although variations and modifications therein may be affected without departing from the spirit and scope of the novel concepts of the disclosure.

It is to be understood that both the foregoing general description and the following detailed description are exemplary and explanatory only and are not restrictive of the invention, as claimed.

DETAILED DESCRIPTION OF THE INVENTION

Figure 1A:
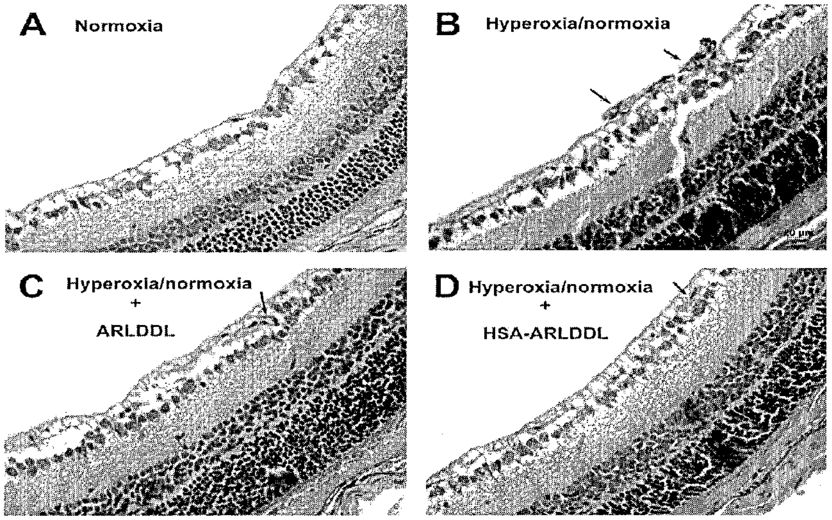
FIG. 1A is a set of four photographs showing angiogenesis in a mouse model of oxygen-induced retinopathy (B), reduced angiogenesis in a oxygen-induced retinopathy mouse treated with ARLDDL rhodostomin variant (C) and reduced angiogenesis in a oxygen-induced retinopathy mouse treated with HSA-ARLDDL rhodostomin variant (D). Photograph (A) is normoxia (control group). Arrows indicate blood vessel profiles (BVPs).

Various embodiments of the invention are now described in detail. As used in the description and throughout the claims, the meaning of "a", "an", and "the" includes plural reference unless the context clearly dictates otherwise. Also, as used in the description and throughout the claims, the meaning of "in" includes "in" and "on" unless the context clearly dictates otherwise. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to the various embodiments given in this specification.

Unless otherwise defined, all technical and scientific terms used herein have the same meaning as commonly understood by one of ordinary skill in the art to which this invention pertains. In the case of conflict, the present document, including definitions will control.

The terms "around," "about" or "approximately" shall generally mean within 20 percent, within 10 percent, within 5, 4, 3, 2 or 1 percent of a given value or range. Numerical quantities given are approximate, meaning that the term "around," "about" or "approximately" can be inferred if not expressly stated.

The terms "peptide" and "protein" are used interchangeably throughout the application.

The terms "low doses" and "low amounts" are used interchangeably throughout the application.

The terms "subject" and "mammal" include, but are not limited to, a human.

The term "treatment" refers to any administration or application of remedies for disease in a mammal and includes inhibiting the disease, arresting its development, relieving the disease, for example, by causing regression, or restoring or repairing a lost, missing, or defective function; or stimulating an inefficient process. The term includes obtaining a desired pharmacologic and/or physiologic effect, covering any treatment of a pathological condition or disorder in a mammal. The effect may be prophylactic in terms of completely or partially preventing a disorder or symptom thereof and/or may be therapeutic in terms of a partial or complete cure for a disorder and/or adverse affect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed in the formulation and is compatible with other ingredients of the formulation.

The term "composition" refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the rhodostomin variant is present in the cells or in the culture medium. For example, compositions for oral administration can form solutions, suspensions, tablets, pills, capsules, sustained release formulations, oral rinses or powders.

The term "angiogenesis-related eye disease" refers to any ocular disease that is related to the growth of new blood vessels from pre-existing vessels. These diseases include but are not limited to, age-related macular degeneration, diabetic retinopathy, corneal neovascularizing diseases, retinal angiomatous proliferation, polypoidal choroidal vasculopathy, ischaemia-induced neovascularizing retinopathy, high myopia and retinopathy of prematurity.

The term "therapeutically effective amount" refers to an amount which, when administered to a living subject, achieves a desired effect on the living subject. The exact amount will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

The term "RGD motif variant" refers to a peptide comprising a modification in the amino acid sequence that spans the RGD sequence of a corresponding wild type sequence, such as the sequence comprising RGD in Rhodostomin.

The term "ARGDDP" refers to a rhodostomin variant having an RGD motif variant $^{48}$ARGDDP$^{53}$. The numbers "48" and "53" refer to positions of these amino acids in the amino acid sequence of wild type rhodostomin. ARGDDP is represented by SEQ ID NO: 1.

The term "ARGDDV" refers to a rhodostomin variant having an RGD motif variant $^{48}$ARGDDV$^{53}$. The numbers "48" and "53" refer to positions of these amino acids in the amino acid sequence of wild type rhodostomin. ARGDDV is represented by SEQ ID NO: 2.

The term "ARGDDL" refers to a rhodostomin variant having an RGD motif variant $^{48}$ARGDDL$^{53}$. The numbers "48" and "53" refer to positions of these amino acids in the amino acid sequence of wild type rhodostomin. ARGDDL is represented by SEQ ID NO: 3.

The term "PRGDDL" refers to a rhodostomin variant having an RGD motif variant $^{48}$PRGDDL$^{53}$. The numbers "48" and "53" refer to positions of these amino acids in the amino acid sequence of wild type rhodostomin. PRGDDL is represented by SEQ ID NO: 4.

The term "ARGDDM" refers to a rhodostomin variant having an RGD motif variant $^{48}$ARGDDM$^{53}$. The numbers "48" and "53" refer to positions of these amino acids in the amino acid sequence of wild type rhodostomin. ARGDDM is represented by SEQ ID NO: 5.

The term "PRGDDM" refers to a rhodostomin variant having an RGD motif variant $^{48}$PRGDDM$^{53}$. The numbers "48" and "53" refer to positions of these amino acids in the amino acid sequence of wild type rhodostomin. PRGDDM is represented by SEQ ID NO: 6.

The term "PRLDMP" refers to a rhodostomin variant having an RGD motif variant $^{48}$PRLDMP$^{53}$. The numbers "48" and "53" refer to positions of these amino acids in the amino acid sequence of wild type rhodostomin. PRLDMP is represented by SEQ ID NO: 7.

The term "PRGDDL" refers to a rhodostomin variant having an RGD motif variant $^{48}$PRLDDL$^{53}$. The numbers "48" and "53" refer to positions of these amino acids in the amino acid sequence of wild type rhodostomin. PRLDDL is represented by SEQ ID NO: 8.

The term "ARLDDL" refers to a rhodostomin variant having an RGD motif variant $^{48}$ARLDDL$^{53}$. The numbers "48" and "53" refer to positions of these amino acids in the amino acid sequence of wild type rhodostomin. ARLDDL is represented by SEQ ID NO: 9.

The term "PRIDMP" refers to a rhodostomin variant having an RGD motif variant $^{48}$PRIDMP$^{53}$. The numbers "48" and "53" refer to positions of these amino acids in the amino acid sequence of wild type rhodostomin. PRIDMP is represented by SEQ ID NO: 10.

The term "PRHDMP" refers to a rhodostomin variant having an RGD motif variant $^{48}$PRHDMP$^{53}$. The numbers "48" and "53" refer to positions of these amino acids in the amino acid sequence of wild type rhodostomin. PRHDMP is represented by SEQ ID NO: 11.

The term "PRGDNP" refers to a rhodostomin variant having an RGD motif variant $^{48}$PRGDNP$^{53}$. The numbers "48" and "53" refer to positions of these amino acids in the amino acid sequence of wild type rhodostomin. PRGDNP is represented by SEQ ID NO: 12.

The term "PRGDGP" refers to a rhodostomin variant having an RGD motif variant $^{48}$PRGDGP$^{53}$. The numbers "48" and "53" refer to positions of these amino acids in the amino acid sequence of wild type rhodostomin. PRGDGP is represented by SEQ ID NO: 13.

The term "HSA-ARLDDL" refers to a fusion protein which comprises a) a human serum albumin (HSA) variant, b) a linker amino acid sequence and c) a rhodostomin variant having an RGD motif variant $^{48}$ARLDDL$^{53}$. It is represented by SEQ ID NO: 14.

The term "HSA(C34S)-ARLDDL" refers to a fusion protein which comprises a) a human serum albumin (HSA) variant wherein the cysteine residue at position 34 of wild type HSA amino acid sequence has been replaced with serine, b) a linker amino acid sequence and c) a rhodostomin variant having an RGD motif variant $^{48}$ARLDDL$^{53}$. It is represented by SEQ ID NO: 15.

The term "HSA(C34A)-ARLDDL" refers to a fusion protein which comprises a) a human serum albumin (HSA) variant wherein the cysteine residue at position 34 of wild type HSA amino acid sequence has been replaced with alanine, b) a linker amino acid sequence, and a rhodostomin variant having an RGD motif variant $^{48}$ARLDDL$^{53}$. It is represented by SEQ ID NO: 16.

It is to be understood that the invention comprises compositions and methods utilizing fusion proteins wherein rhodostomin variants other than ARLDDL are fused to an HSA variant through a linker amino acid sequence. For example, fusion proteins suitable for the purposes of the invention include, but are not limited to, HSA-ARGDDP, HSA(C34S)-ARGDDP, HSA(C34A)-ARGDDP, HSA-ARGDDV, HSA (C34S)-ARGDDV, HSA(C34A)-ARGDDV, and etc.

Compositions and Methods of the Invention

The inventors expressly incorporate by reference all of the methods and rhodostomin variants disclosed in the patent application U.S. Ser. No. 61/226,945.

Generally, the invention relates to compositions and methods for the treatment of an angiogenesis-related eye disease utilizing low doses of rhodostomin variants.

The term "low doses" refers to the doses which are lower than those conventionally used for the treatment of an angiogenesis-related eye disease.

Preferably, "low doses" are from about 0.0001 pg to about 300 ug; more preferably, from about 0.0005 pg to about 200 ug, and even more preferably, from about 0.001 pg to about 100 ug of the rhodostomin variants suitable for the purposes of the present invention. The doses can be administered to a subject in need thereof as either single doses or divided doses as long as the total administered dose is within the provided range.

Preferably, said rhodostomin variants are fused with human serum albumin (HSA) or variants of HSA which may be pegylated or otherwise modified.

Even more preferably, a rhodostomin variant suitable for the purposes of the present invention is selected from a rhodostomin variant comprising an amino acid sequence selected from SEQ ID NO: 1 through SEQ ID NO: 16, or a pharmaceutically acceptable salt of said rhodostomin variant.

In a preferred embodiment, the rhodostomin variants are conjugated with albumin or pegylated.

Even more preferably, the rhodostomin variants suitable for the purposes of the present invention comprise SEQ ID NO: 9 or SEQ ID NO: 15.

The most preferred rhodostomin variant for the purposes of the present invention is HSA(C34S)-ARLDDL, which is represented by SEQ ID NO: 15. HSA-ARLDDL C34S is a recombinant protein comprising a rhodostomin variant with an RGD motif $^{48}$ARLDDL$^{53}$, wherein the rhodostomin variant is conjugated with a variant of Human Serum Albumin (HSA). HSA(C34S)-ARLDDL is selective for $\alpha v\beta 3$ integrin and exhibits reduced binding to $\alpha IIb\beta 3$ and/or $\alpha 5\beta 1$ integrin as compared to a wild-type rhodostomin.

In one embodiment, the invention relates to a composition for the treatment and/or prevention of an angiogenesis-related eye disease comprising from about 0.0001 pg to about 300 ug of a rhodostomin variant comprising an amino acid sequence selected from SEQ ID NO: 1 through SEQ ID NO: 16, or a pharmaceutically acceptable salt of said rhodostomin variant.

Preferably, the compositions of the invention comprise from about 0.0005 pg to about 200 ug, and more preferably, from about 0.001 pg to about 100 ug of the rhodostomin variant suitable for the purposes of the invention.

In one embodiment, the compositions of the invention are formulated as topical compositions. In another embodiment, the compositions of the invention are suitable for an intravitreous injection (i.e., into the eye).

In another embodiment, the invention relates to a method for the treatment and/or prevention of an angiogenesis-related eye disease comprising administering to a subject in need thereof from about 0.0001 pg to about 300 ug per eye of said subject of a rhodostomin variant comprising an amino acid sequence selected from SEQ ID NO: 1 through SEQ ID NO: 16, or a pharmaceutically acceptable salt of said rhodostomin variant.

In a preferred embodiment, the invention relates to a method for the treatment and/or prevention of an angiogenesis-related eye disease comprising administering to a subject in need thereof from about 0.0001 pg to about 300 ug per eye of said subject of a rhodostomin variant comprising an amino acid sequence selected from SEQ ID NO: 9 and SEQ ID NO: 15, or a pharmaceutically acceptable salt of said rhodostomin variant.

In a more preferred embodiment, the invention relates to a method for the treatment and/or prevention of an angiogenesis-related eye disease comprising administering to a subject in need thereof from about 0.0005 pg to about 200 ug per eye of said subject of a rhodostomin variant comprising an amino acid sequence selected from SEQ ID NO: 1 through SEQ ID NO: 16, or a pharmaceutically acceptable salt of said rhodostomin variant.

In an even more preferred embodiment, the invention relates to a method for the treatment and/or prevention of an angiogenesis-related eye disease comprising administering to a subject in need thereof from about 0.001 pg to about 100 ug per eye of said subject of a rhodostomin variant comprising an amino acid sequence selected from SEQ ID NO: 1 through SEQ ID NO: 16, or a pharmaceutically acceptable salt of said rhodostomin variant.

Preferably, the methods of the invention comprise administering from about 0.005 pg to about 200 ug, and more preferably, from about 0.001 pg to about 100 ug of a rhodostomin variant suitable for the purposes of the invention per eye of said subject.

In one embodiment, the methods of the invention comprise administering a rhodostomin variant suitable for the purposes of the invention through an intraocular injection to said subject.

In one embodiment, the angiogenesis-related eye disease is selected from the group consisting of age-related macular degeneration, diabetic retinopathy, corneal neovascularizing diseases, retinal angiomatous proliferation, polypoidal choroidal vasculopathy, age-related ischaemia-induced neovascularizing retinopathy, high myopia and retinopathy of prematurity.

The compositions of the invention may be administered to a subject in need of treatment by injection systemically, such as by intravitreous injection or intravenous injection; or by injection or application to the relevant site, such as by direct injection, or direct application to the site when the site is exposed in surgery; or by topical application.

The compositions of the invention can be used in combination with another active agent to treat angiogenesis-related eye diseases.

Thus, in one embodiment, the method of treatment and/or prevention of an angiogenesis-related eye disease further comprises administering to a subject another active agent.

Preferably, the other active agent is selected from the group consisting of VEGF antagonists, anti-angiogenesis agents, anti-inflammation agents, and steroids.

Administration of the active agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, intramuscular injection, intravitreous injection (i.e., into the eye), topical application, including but not limited to eye drops, creams, and emulsions, implantation and inhalation.

Pharmaceutical compositions of the invention may be provided as formulations with pharmaceutically acceptable carriers, excipients and diluents, which are known in the art. These pharmaceutical carriers, excipients and diluents include those listed in the USP pharmaceutical excipients listing. USP and NF Excipients, Listed by Categories, p. 2404-2406, USP 24 NF 19, United States Pharmacopeial Convention Inc., Rockville, Md. (ISBN 1-889788-03-1). Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable carriers include, but are not limited to, water, dextrose, glycerol, saline, ethanol, and combinations thereof. The carrier can contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as antioxidants, humectants, viscosity stabilizers, and similar agents can be added as necessary. Percutaneous penetration enhancers such as Azone can also be included.

The rhodostomin variants suitable for the purposes of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Other formulations for oral or parenteral delivery can also be used, as conventional in the art.

The pharmaceutical compositions of the invention can be formulated into preparations in solid, semi-solid, liquid or gaseous forms, such as tablets, capsules, powders, granules, ointments, solutions, suppositories, injections, inhalants and aerosols.

In pharmaceutical dosage forms, the compositions of the invention can be administered in the form of their pharmaceutically acceptable salts, or they can also be used alone or in appropriate association, as well as in combination, with other pharmaceutically active compounds. The subject compositions are formulated in accordance to the mode of potential administration.

The present invention is more particularly described in the following examples that are intended as illustrative only, since many modifications and variations therein will be apparent to those skilled in the art.

EXAMPLE 1

Figure 1B:
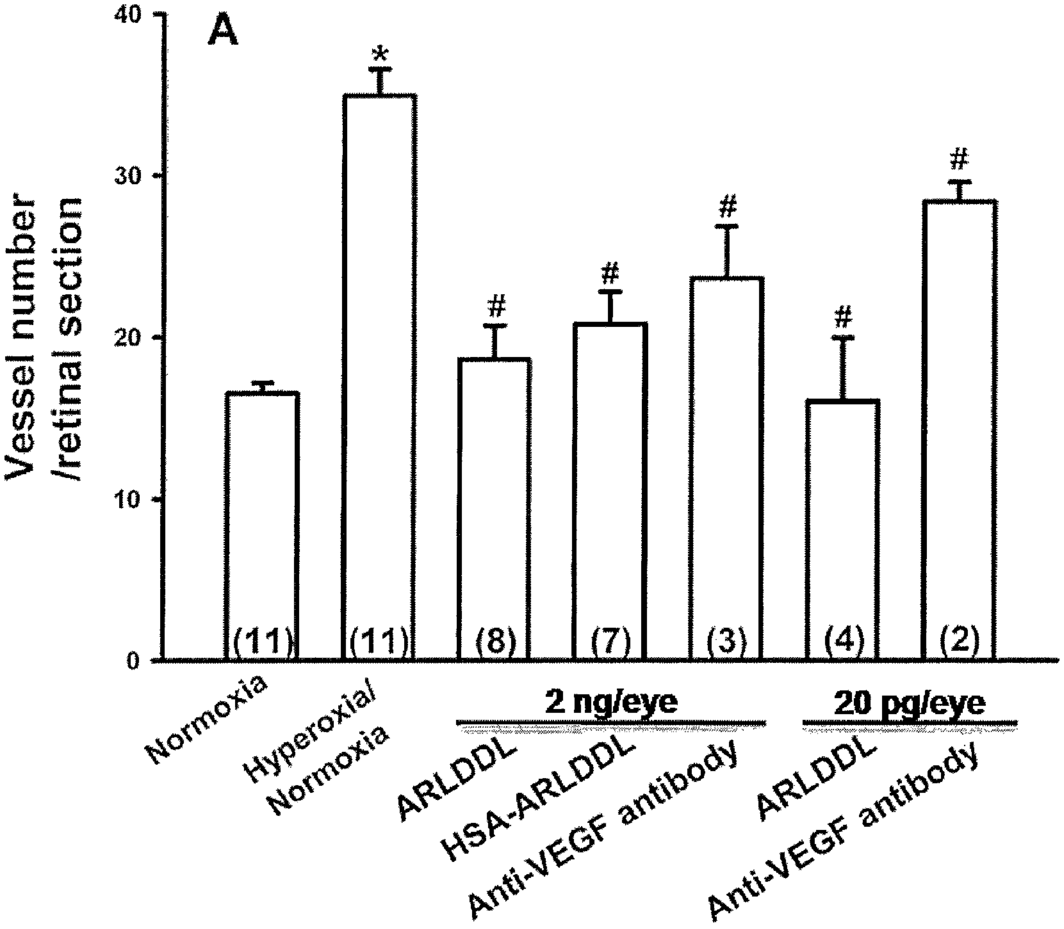
FIG. 1B is a graph showing reduced number of vessels per retinal section in a mouse model of oxygen-induced retinopathy treated with ARLDDL rhodostomin variant or HSA-ARLDDL rhodostomin variant.

Inhibition of Angiogenesis in Retina by ARLDDL and HSA-ARLDDL in a Mouse Model of Oxygen-Induced Retinopathy An animal model for oxygen-induced retinopathy in mice was generated as follows. 7-day-old mice with at least two nursing dams per group were assigned to an oxygen chamber containing 75% oxygen (Hyperoxia) or to room air (Normoxia). The mice were exposed to less than 300 lux of 12-hour cyclical broad spectrum light. Surrogate dams were substituted if nursing dams died. The oxygen-treated mice were housed in an incubator connected to a Bird 3-M oxygen blender (Palm Springs, Calif.) with oxygen and nitrogen, allowing adjustment of oxygen concentration to 75%±2%. A flow rate of 1.5 L/min was checked twice daily. Oxygen concentration was monitored with a Beckman oxygen analyzer (Model D2, Irvine, Calif.). The cage temperature was maintained at 23° C.±2° C. The mice were placed in the oxygen chamber with enough food and water to sustain them for 5 days. The chamber was not opened during hyperoxia exposure from Day 1 to Day 5. On Day 5, the animals were returned to room air for 7 days. Once the oxygen-treated mice returned to room air, normal saline (2 μl/eye), ARLDDL (2 ng/eye or 20 pg/eye), HSA-ARLDDL (2 ng/eye), or anti-VEGF antibody (2 ng/eye or 20 pg/eye) was administered via intravitreous injection on Day 5 and the mice were sacrificed on Day 12. Sections from one of the eyes of each animal were made, deparaffinized, and stained with hematoxylin and eosin. Vessel number per retinal section was counted in the inner retina, and included vessels adherent to the inner limiting membrane. Counting was performed on a photomicroscope (Leica) at a magnification of 100×. The results are shown in FIG. 1B.

The results demonstrate that ARLDDL and HSA-ARLDDL at doses of 2 ng/eye and 20 pg/eye reduced the vessel number per retinal section as compared to normal saline treated group. Further, even at a very low dose of 20 pg/eye, ARLDDL resulted in a greater reduction of the vessel number per retinal section as compared to 2 ng/eye of ARLDDL, 2 ng/eye of HSA-ARLDDL and 20 pg/eye of an anti-VEGF antibody.

Figure 1C:
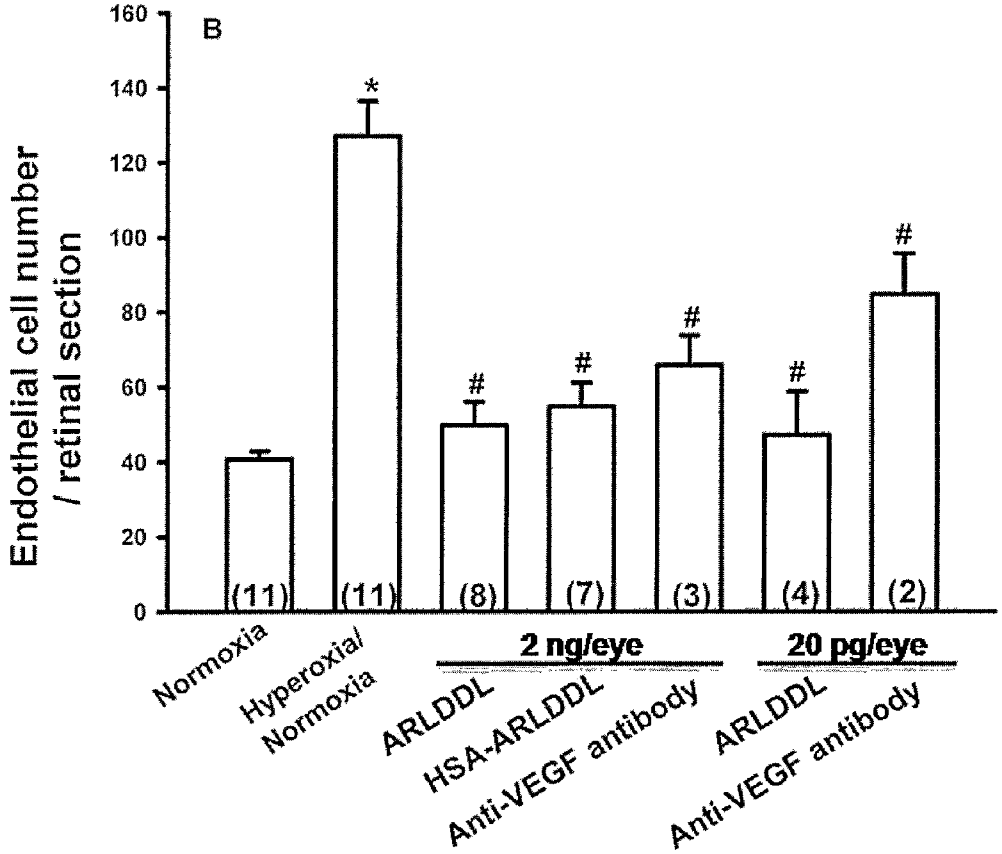
FIG. 1C is a graph showing reduced number of endothelial cells per retinal section in a mouse model of oxygen-induced retinopathy treated with ARLDDL rhodostomin variant or HSA-ARLDDL rhodostomin variant.

Endothelial cells were counted in the anterior part of the ganglion cell layer and on inner limiting membrane of the retina by a person blinded to the same identity. The results are shown in FIG. 1C.

The results demonstrate that ARLDDL and HSA-ARLDDL at both doses of 2 ng/eye and 20 pg/eye reduced the endothelial cell number per retinal section.

EXAMPLE 2

Figure 2A:
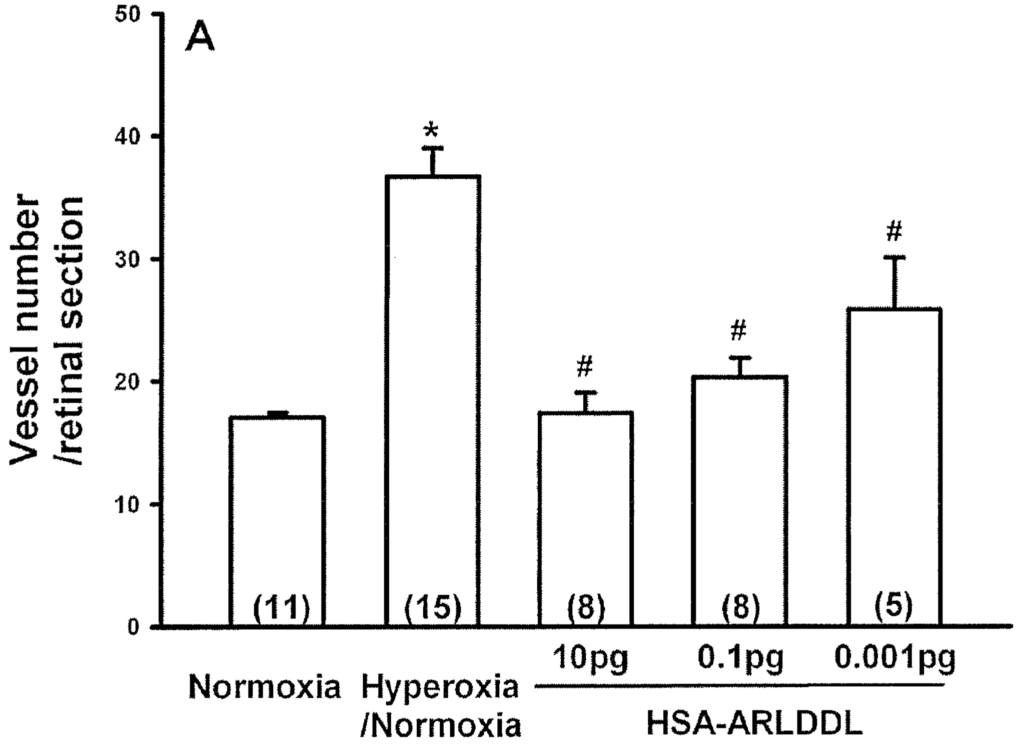
FIG. 2A is a graph showing reduced number of vessels per retina section in a mouse model of oxygen-induced retinopathy treated with HSA-ARLDDL rhodostomin variant at the following amounts: 10 pg, 0.1 pg and 0.001 pg.

Inhibition of Angiogenesis in Retina by Very Low Doses of ARLDDL and HSA-ARLDDL in a Mouse Model of Oxygen-Induced Retinopathy An animal model for oxygen-induced retinopathy in mice was generated as described in EXAMPLE 1. The following amounts of HSA-ARLDDL: 10 pg/eye, 0.1 pg/eye and 0.001 pg/eye were administered via intravitreous injection and the treated mice were sacrificed on Day 12. Sections from one of the eyes of each animal were made, deparaffinized, and stained with hematoxylin and eosin. Vessel number per retinal section was counted in the inner retina, and included vessels adherent to the inner limiting membrane. Counting was performed on a photomicroscope (Leica) at a magnification of 100×. The results are shown in FIG. 2A.

The results demonstrate that HSA-ARLDDL at 10 pg, 0.1 pg and 0.001 pg per eye reduced the vessel number per retinal section as compared to the normal saline treated group.

Figure 2B:
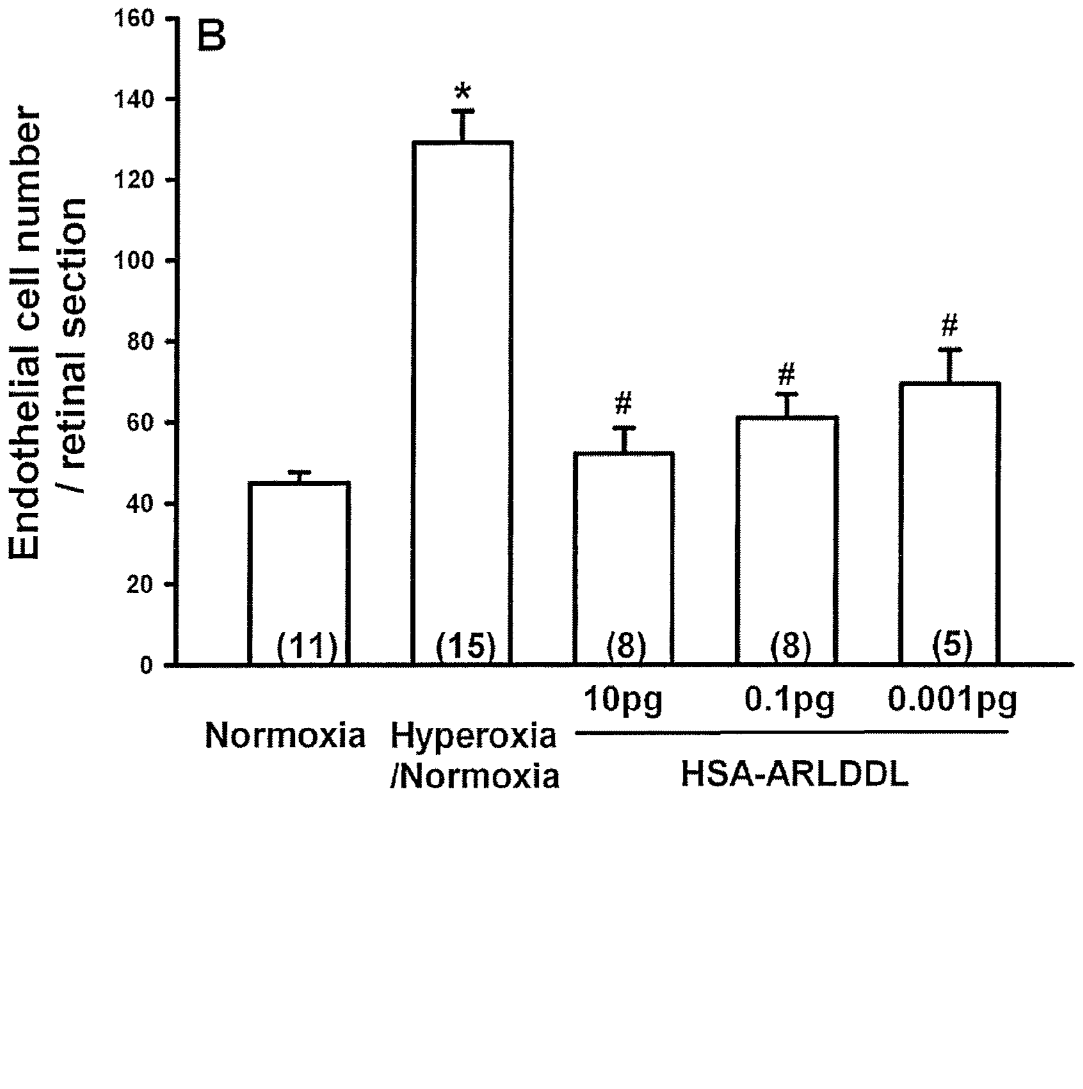
FIG. 2B is a graph showing reduced number of endothelial cells per retina section in a mouse model of oxygen-induced retinopathy treated with ARLDDL rhodostomin variant or HSA-ARLDDL rhodostomin variant at the following amounts: 10 pg, 0.1 pg and 0.001 pg.

Endothelial cells were counted in the anterior part of the ganglion cell layer and on inner limiting membrane of the retina by a person blinded to the same identity. The results are shown in FIG. 2B.

The results demonstrate that HSA-ARLDDL at 10 pg, 0.1 pg and 0.001 pg per eye reduced the endothelial cell number per retinal section as compared to the normal saline treated group.

EXAMPLE 3

Inhibition of Angiogenesis in Retina by HSA-ARLDDL Versus Avastin® in a Mouse Model of Oxygen-Induced Retinopathy An animal model for hyperoxia/normoxia in mice was generated as described in EXAMPLE 1. ARLDDL (10 pg/eye or 0.1 pg/eye) or Avastin® (20 pg/eye or 0.2 pg/eye) was administered via intravitreous injection and the treated mice were sacrificed on Day 12.

Figure 3A:
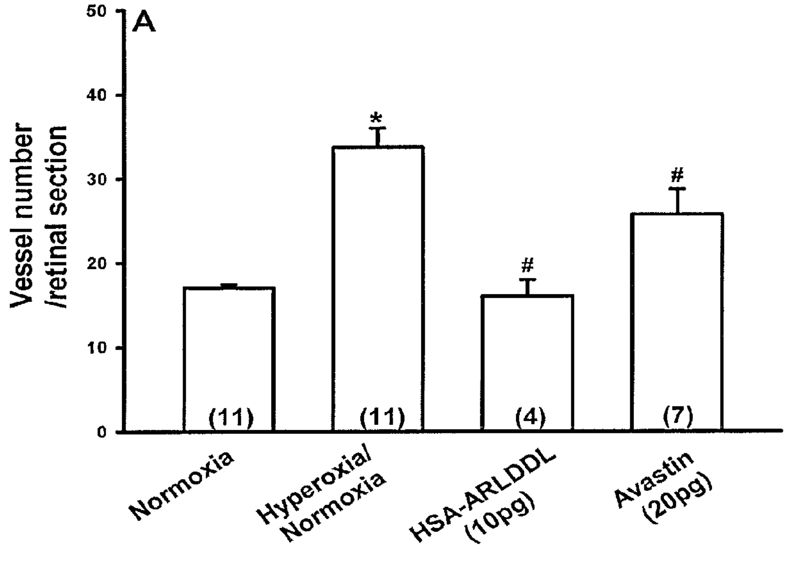
FIG. 3A is a graph showing reduced number of vessels/retina section in a mouse model of oxygen-induced retinopathy treated with HSA-ARLDDL rhodostomin variant as compared to a oxygen-induced retinopathy mouse treated with Avastin®.
Figure 3:
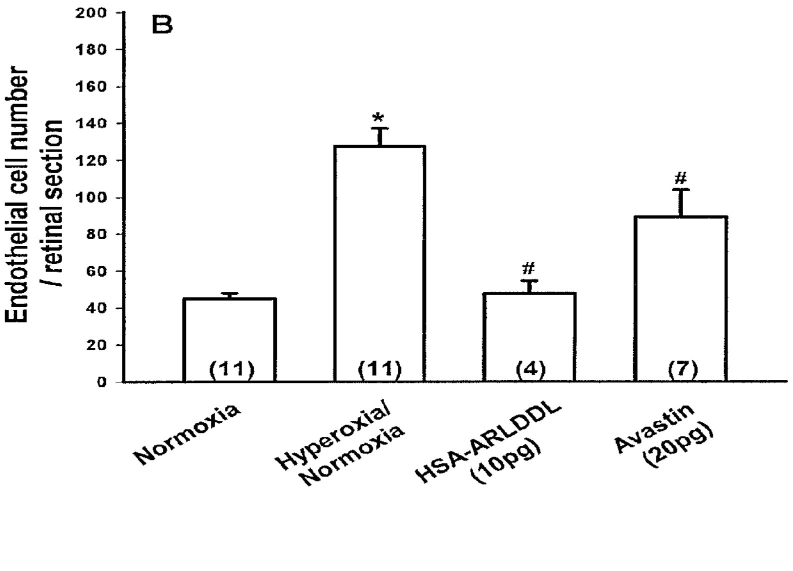
FIG. 3B is a graph showing reduced number of endothelial cells/retina section in a mouse model of oxygen-induced retinopathy treated with HSA-ARLDDL rhodostomin variant as compared to a oxygen-induced retinopathy mouse treated with Avastin®.
Figure 4A:
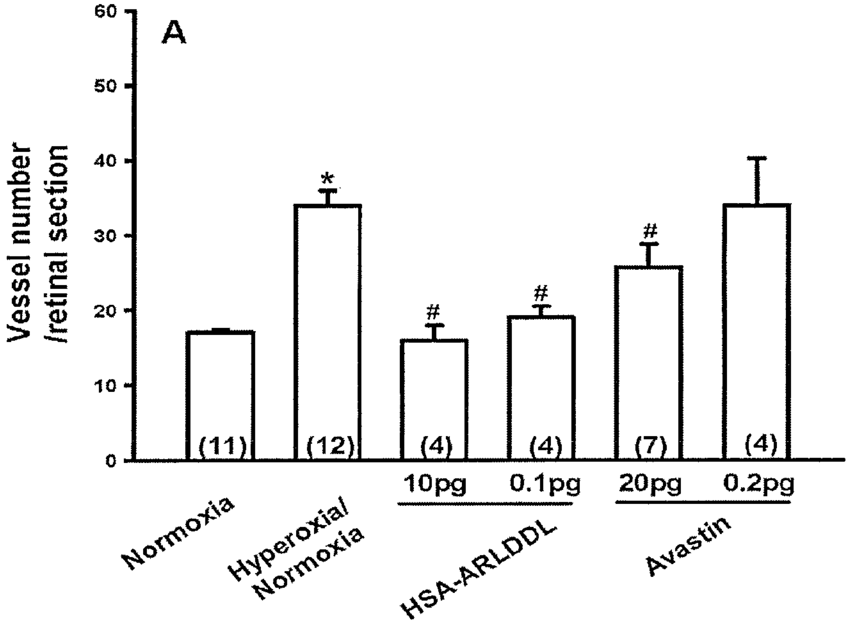
FIG. 4A is a graph showing reduced number of vessels/retina section in a mouse model of oxygen-induced retinopathy treated with HSA-ARLDDL rhodostomin variant as compared to a oxygen-induced retinopathy mouse treated with Avastin®.

Sections from one of the eyes of each animal were made, deparaffinized, and stained with hematoxylin and eosin. Vessel number per retinal section was counted in the inner retina, and included vessels adherent to the inner limiting membrane. Counting was performed on a photomicroscope (Leics) at a magnification of 100×. The results are shown in FIGS. 3A and 4A.

Figure 4B:
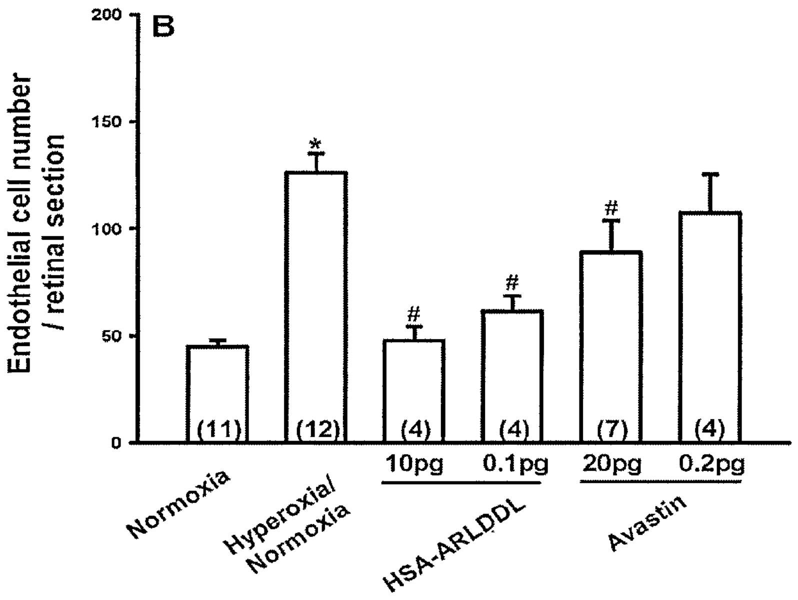
FIG. 4B is a graph showing reduced number of endothelial cells/retina section in a mouse model of oxygen-induced retinopathy treated with HSA-ARLDDL rhodostomin variant as compared to a oxygen-induced retinopathy mouse treated with Avastin®.

Endothelial cells were counted in the anterior part of the ganglion cell layer and on the inner limiting membrane of the retina by a person blinded to the same identity. The results are shown in FIGS. 3B and 4B.

The results demonstrate that HSA-ARLDDL at all administered dosages was significantly more effective than Avastin® in inhibiting of angiogenesis in retina.

Amino Acid and Nucleotide Sequences Used in the Application

SEQ ID NO: 1 represents an amino acid sequence of "ARGDDP" rhodostomin variant.

SEQ ID NO: 2 represents an amino acid sequence of "ARGDDV" rhodostomin variant.

SEQ ID NO: 3 represents an amino acid sequence of "ARGDDL" rhodostomin variant.

SEQ ID NO: 4 represents an amino acid sequence of "PRGDDL" rhodostomin variant.

SEQ ID NO: 5 represents an amino acid sequence of "ARGDDM" rhodostomin variant.

SEQ ID NO: 6 represents an amino acid sequence of "PRGDDM" rhodostomin variant.

SEQ ID NO: 7 represents an amino acid sequence of "PRLDMP" rhodostomin variant.

SEQ ID NO: 8 represents an amino acid sequence of "PRLDDL" rhodostomin variant.

SEQ ID NO: 9 represents an amino acid sequence of "ARLDDL" rhodostomin variant.

SEQ ID NO: 10 represents an amino acid sequence of "PRIDMP" rhodostomin variant.

SEQ ID NO: 11 represents an amino acid sequence of "PRHDMP" rhodostomin variant.

SEQ ID NO: 12 represents an amino acid sequence of "PRGDNP" rhodostomin variant.

SEQ ID NO: 13 represents an amino acid sequence of "PRGDGP" rhodostomin variant.

SEQ ID NO: 14 represents an amino acid sequence of "HSA-ARLDDL" rhodostomin variant.

SEQ ID NO: 15 represents an amino acid sequence of "HSA(C34S)-ARLDDL" rhodostomin variant.

SEQ ID NO: 16 represents an amino acid sequence of "HSA(C34A)-ARLDDL" rhodostomin variant.

The foregoing description of the exemplary embodiments of the invention has been presented only for the purposes of illustration and description and is not intended to be exhaustive or to limit the invention to the precise forms disclosed. Many modifications and variations are possible in light of the above teaching.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for the treatment of an angiogenesis-related eye disease comprising administering to a human in need thereof between about 0.0001 pg to about 300 pg per eye of a rhodostomin variant comprising an amino acid sequence of SEQ ID NO: 15, or a pharmaceutically acceptable salt of said rhodostomin variant, wherein said angiogenesis-related eye disease is selected from the group consisting of age-related macular degeneration, diabetic retinopathy, corneal neovascularizing diseases, retinal angiomatous proliferation, polypoidal choroidal vasculopathy, age-related ischaemia-induced neovascularizing retinopathy, retinopathy of prematurity, and high myopia.

2. The method of claim 1, wherein said angiogenesis-related eye disease is age-related macular degeneration.

3. The method of claim 1, wherein said angiogenesis-related eye disease is diabetic retinopathy.

4. The method of claim 1, wherein said rhodostomin variant is applied topically to an eye of said human.

5. The method of claim 1, wherein said rhodostomin variant is applied via an intravitreous injection to an eye of said human.

6. The method of claim 1, further comprising administering to said human a therapeutically effective amount of another active agent.

7. The method of claim 6, wherein said another active agent is selected from the group consisting of VEGF antagonists, anti-angiogenesis agents, anti-inflammation agents, and steroids.

8. The method of claim 6, wherein said other active agent is administered concurrently with said rhodostomin variant.

9. The method of claim 6, wherein said other active agent is administered prior to administering said rhodostomin variant.

10. The method of claim 6, wherein said other active agent is administered after administering said rhodostomin variant.

* * * * *

SEQUENCE LISTING

```
<160> NUMBER OF SEQ ID NOS: 16

<210> SEQ ID NO 1
<211> LENGTH: 68
<212> TYPE: PRT
<213> ORGANISM: Artificial Sequence
```

-continued

<220> FEATURE:
<223> OTHER INFORMATION: Description of Artificial Sequence: ARGDDP
Synthetic rhodostomin variant

<400> SEQUENCE: 1

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Ala
35 40 45

Arg Gly Asp Asp Pro Asp Asp Arg Cys Thr Gly Gln Ser Ala Asp Cys
50 55 60

Pro Arg Tyr His
65

<210> SEQ ID NO 2
<211> LENGTH: 68
<212> TYPE: PRT
<213> ORGANISM: Artificial Sequence
<220> FEATURE:
<223> OTHER INFORMATION: Description of Artificial Sequence: ARGDDV
Synthetic rhodostomin variant

<400> SEQUENCE: 2

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Ala
35 40 45

Arg Gly Asp Asp Val Asp Asp Arg Cys Thr Gly Gln Ser Ala Asp Cys
50 55 60

Pro Arg Tyr His
65

<210> SEQ ID NO 3
<211> LENGTH: 68
<212> TYPE: PRT
<213> ORGANISM: Artificial Sequence
<220> FEATURE:
<223> OTHER INFORMATION: Description of Artificial Sequence: ARGDDL
Synthetic rhodostomin variant

<400> SEQUENCE: 3

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Ala
35 40 45

Arg Gly Asp Asp Leu Asp Asp Arg Cys Thr Gly Gln Ser Ala Asp Cys
50 55 60

Pro Arg Tyr His
65

<210> SEQ ID NO 4
<211> LENGTH: 68
<212> TYPE: PRT
<213> ORGANISM: Artificial Sequence
<220> FEATURE:

-continued

```
<223> OTHER INFORMATION: Description of Artificial Sequence: PRGDDL
      Synthetic rhodostomin variant

<400> SEQUENCE: 4

Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
         35                  40                  45

Arg Gly Asp Asp Leu Asp Asp Arg Cys Thr Gly Gln Ser Ala Asp Cys
     50                  55                  60

Pro Arg Tyr His
 65


<210> SEQ ID NO 5
<211> LENGTH: 68
<212> TYPE: PRT
<213> ORGANISM: Artificial Sequence
<220> FEATURE:
<223> OTHER INFORMATION: Description of Artificial Sequence: ARGDDM
      Synthetic rhodostomin variant

<400> SEQUENCE: 5

Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Ala
         35                  40                  45

Arg Gly Asp Asp Met Asp Asp Arg Cys Thr Gly Gln Ser Ala Asp Cys
     50                  55                  60

Pro Arg Tyr His
 65


<210> SEQ ID NO 6
<211> LENGTH: 68
<212> TYPE: PRT
<213> ORGANISM: Artificial Sequence
<220> FEATURE:
<223> OTHER INFORMATION: Description of Artificial Sequence: PRGDDM
      Synthetic rhodostomin variant

<400> SEQUENCE: 6

Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
         35                  40                  45

Arg Gly Asp Asp Met Asp Asp Arg Cys Thr Gly Gln Ser Ala Asp Cys
     50                  55                  60

Pro Arg Tyr His
 65


<210> SEQ ID NO 7
<211> LENGTH: 68
<212> TYPE: PRT
<213> ORGANISM: Artificial Sequence
<220> FEATURE:
<223> OTHER INFORMATION: Description of Artificial Sequence: PRLDMP
```

Synthetic rhodostomin variant

<400> SEQUENCE: 7

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Pro
35 40 45

Arg Leu Asp Met Pro Asp Asp Arg Cys Thr Gly Gln Ser Ala Asp Cys
50 55 60

Pro Arg Tyr His
65

<210> SEQ ID NO 8
<211> LENGTH: 68
<212> TYPE: PRT
<213> ORGANISM: Artificial Sequence
<220> FEATURE:
<223> OTHER INFORMATION: Description of Artificial Sequence: PRLDDL
Synthetic rhodostomin variant

<400> SEQUENCE: 8

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Pro
35 40 45

Arg Leu Asp Asp Leu Asp Asp Arg Cys Thr Gly Gln Ser Ala Asp Cys
50 55 60

Pro Arg Tyr His
65

<210> SEQ ID NO 9
<211> LENGTH: 68
<212> TYPE: PRT
<213> ORGANISM: Artificial Sequence
<220> FEATURE:
<223> OTHER INFORMATION: Description of Artificial Sequence: ARLDDL
Synthetic rhodostomin variant

<400> SEQUENCE: 9

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Ala
35 40 45

Arg Leu Asp Asp Leu Asp Asp Arg Cys Thr Gly Gln Ser Ala Asp Cys
50 55 60

Pro Arg Tyr His
65

<210> SEQ ID NO 10
<211> LENGTH: 68
<212> TYPE: PRT
<213> ORGANISM: Artificial Sequence
<220> FEATURE:
<223> OTHER INFORMATION: Description of Artificial Sequence: PRIDMP
Synthetic rhodostomin variant -continued

<400> SEQUENCE: 10

```
Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
         35                  40                  45

Arg Ile Asp Met Pro Asp Asp Arg Cys Thr Gly Gln Ser Ala Asp Cys
     50                  55                  60

Pro Arg Tyr His
 65
```

<210> SEQ ID NO 11
<211> LENGTH: 68
<212> TYPE: PRT
<213> ORGANISM: Artificial Sequence
<220> FEATURE:
<223> OTHER INFORMATION: Description of Artificial Sequence: PRHDMP
      Synthetic rhodostomin variant

<400> SEQUENCE: 11

```
Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
         35                  40                  45

Arg His Asp Met Pro Asp Asp Arg Cys Thr Gly Gln Ser Ala Asp Cys
     50                  55                  60

Pro Arg Tyr His
 65
```

<210> SEQ ID NO 12
<211> LENGTH: 68
<212> TYPE: PRT
<213> ORGANISM: Artificial Sequence
<220> FEATURE:
<223> OTHER INFORMATION: Description of Artificial Sequence: PRGDNP
      Synthetic rhodostomin variant

<400> SEQUENCE: 12

```
Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
         35                  40                  45

Arg Gly Asp Asn Pro Asp Asp Arg Cys Thr Gly Gln Ser Ala Asp Cys
     50                  55                  60

Pro Arg Tyr His
 65
```

<210> SEQ ID NO 13
<211> LENGTH: 68
<212> TYPE: PRT
<213> ORGANISM: Artificial Sequence
<220> FEATURE:
<223> OTHER INFORMATION: Description of Artificial Sequence: PRGDGP
      Synthetic rhodostomin variant

<400> SEQUENCE: 13

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Pro
35 40 45

Arg Gly Asp Gly Pro Asp Asp Arg Cys Thr Gly Gln Ser Ala Asp Cys
50 55 60

Pro Arg Tyr His
65

<210> SEQ ID NO 14
<211> LENGTH: 670
<212> TYPE: PRT
<213> ORGANISM: Artificial Sequence
<220> FEATURE:
<223> OTHER INFORMATION: Description of Artificial Sequence: HSA-ARLDDL

<400> SEQUENCE: 14

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Cys Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

Arg Ala Phe Lys Ala Trp Ala Val Ala Arg Leu Ser Gln Arg Phe Pro
210 215 220

Lys Ala Glu Phe Ala Glu Val Ser Lys Leu Val Thr Asp Leu Thr Lys
225 230 235 240

Val His Thr Glu Cys Cys His Gly Asp Leu Leu Glu Cys Ala Asp Asp
245 250 255

Arg Ala Asp Leu Ala Lys Tyr Ile Cys Glu Asn Gln Asp Ser Ile Ser
260 265 270

Ser Lys Leu Lys Glu Cys Cys Glu Lys Pro Leu Leu Glu Lys Ser His

-continued

```
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Thr Gly Gly Gly Gly Ser
            580                 585                 590

Gly Gly Gly Gly Ser Gly Gly Gly Gly Ser Gly Lys Glu Cys Asp Cys
        595                 600                 605

Ser Ser Pro Glu Asn Pro Cys Cys Asp Ala Ala Thr Cys Lys Leu Arg
    610                 615                 620

Pro Gly Ala Gln Cys Gly Glu Gly Leu Cys Cys Glu Gln Cys Lys Phe
625                 630                 635                 640

Ser Arg Ala Gly Lys Ile Cys Arg Ile Ala Arg Leu Asp Asp Leu Asp
                645                 650                 655

Asp Arg Cys Thr Gly Gln Ser Ala Asp Cys Pro Arg Tyr His
            660                 665                 670
```

<210> SEQ ID NO 15
<211> LENGTH: 670
<212> TYPE: PRT
<213> ORGANISM: Artificial Sequence
<220> FEATURE:
<223> OTHER INFORMATION: Description of Artificial Sequence: Synthetic
HSA-ARLDDL C34S

<400> SEQUENCE: 15

```
Asp Ala His Lys Ser Glu Val Ala His Arg Phe Lys Asp Leu Gly Glu
  1               5                  10                  15

Glu Asn Phe Lys Ala Leu Val Leu Ile Ala Phe Ala Gln Tyr Leu Gln
             20                  25                  30

Gln Ser Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
     50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
```

-continued

```
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Thr Gly Gly Gly Gly Ser
            580                 585                 590

Gly Gly Gly Gly Ser Gly Gly Gly Gly Ser Gly Lys Glu Cys Asp Cys
        595                 600                 605

Ser Ser Pro Glu Asn Pro Cys Cys Asp Ala Ala Thr Cys Lys Leu Arg
    610                 615                 620

Pro Gly Ala Gln Cys Gly Glu Gly Leu Cys Cys Glu Gln Cys Lys Phe
625                 630                 635                 640

Ser Arg Ala Gly Lys Ile Cys Arg Ile Ala Arg Leu Asp Asp Leu Asp
                645                 650                 655

Asp Arg Cys Thr Gly Gln Ser Ala Asp Cys Pro Arg Tyr His
            660                 665                 670


<210> SEQ ID NO 16
<211> LENGTH: 670
<212> TYPE: PRT
<213> ORGANISM: Artificial Sequence
<220> FEATURE:
<223> OTHER INFORMATION: Description of Artificial Sequence: Synthetic
      HSA-ARLDDL C34A Mutant

<400> SEQUENCE: 16

Asp Ala His Lys Ser Glu Val Ala His Arg Phe Lys Asp Leu Gly Glu
  1               5                  10                  15

Glu Asn Phe Lys Ala Leu Val Leu Ile Ala Phe Ala Gln Tyr Leu Gln
             20                  25                  30

Gln Ala Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
     50                  55                  60

Ser Leu His Thr Leu Phe Gly Asp Lys Leu Cys Thr Val Ala Thr Leu
 65                  70                  75                  80
```

-continued

```
Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
```

-continued

```
                500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Thr Gly Gly Gly Gly Ser
            580                 585                 590

Gly Gly Gly Gly Ser Gly Gly Gly Gly Ser Gly Lys Glu Cys Asp Cys
        595                 600                 605

Ser Ser Pro Glu Asn Pro Cys Cys Asp Ala Ala Thr Cys Lys Leu Arg
    610                 615                 620

Pro Gly Ala Gln Cys Gly Glu Gly Leu Cys Cys Glu Gln Cys Lys Phe
625                 630                 635                 640

Ser Arg Ala Gly Lys Ile Cys Arg Ile Ala Arg Leu Asp Asp Leu Asp
                645                 650                 655

Asp Arg Cys Thr Gly Gln Ser Ala Asp Cys Pro Arg Tyr His
            660                 665                 670
```